United States Patent
Perovitch et al.

(10) Patent No.: US 9,161,910 B2
(45) Date of Patent: *Oct. 20, 2015

(54) METHOD AND PHARMACEUTICAL COMPOSITIONS FOR TRANS-BUCCAL MUCOSA TREATMENT OF POSTPRANDIAL HYPERGLYCAEMIA IN TYPE II DIABETES

(76) Inventors: Philippe Perovitch, Le Temple (FR); Marc Maury, Saint Medard en Jalles (FR); Jean-Pierre Dumonteix, Villenave d'Ornon (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/383,101

(22) PCT Filed: Jul. 7, 2010

(86) PCT No.: PCT/FR2010/051426
§ 371 (c)(1),
(2), (4) Date: Mar. 26, 2012

(87) PCT Pub. No.: WO2011/004117
PCT Pub. Date: Jan. 13, 2011

(65) Prior Publication Data
US 2012/0190618 A1 Jul. 26, 2012

(30) Foreign Application Priority Data
Jul. 10, 2009 (FR) ...................................... 09 54819

(51) Int. Cl.
A61K 9/00 (2006.01)
A61K 38/22 (2006.01)
A61P 3/10 (2006.01)
A61K 31/63 (2006.01)
A61K 47/10 (2006.01)

(52) U.S. Cl.
CPC .................. *A61K 9/006* (2013.01); *A61K 31/63* (2013.01); *A61K 47/10* (2013.01)

(58) Field of Classification Search
CPC ..... A61K 9/006; A61K 9/0053; A61K 31/63; A61K 31/64; A61K 38/00; A61K 47/10
See application file for complete search history.

(56) References Cited

U.S. PATENT DOCUMENTS

| | | | |
|---|---|---|---|
| 6,451,286 B1 | 9/2002 | Modi | |
| 7,411,089 B2 * | 8/2008 | Koguchi et al. | 562/445 |
| 2003/0235595 A1 * | 12/2003 | Chen et al. | 424/400 |
| 2010/0022496 A1 | 1/2010 | Perovitch et al. | |

FOREIGN PATENT DOCUMENTS

| | | |
|---|---|---|
| WO | WO 2004/019903 A1 | 3/2004 |
| WO | WO 2008/035020 A2 | 3/2008 |

OTHER PUBLICATIONS

Naidoo et al, Effects of Gliclazide Dose Escalation on Postprandial Hyperglycemia in Type 2 Diabetes Mellitus: A Prospective, Open-Label, Case-Controlled, Dose-Escalation Study, Curr Ther Res Clin Exp, 2006, 67, pages 81-102.*
Rendell et al, Targeting postprandial hyperglycemia, Metabolism Clinical and Experimental, 2006, 55, pp. 1263-1281.*
Database Embase [Online] Elsevier Science Publishers, Amsterdam, NL; 1977, Yokosuka T et al: "Nasal and sublingual administration of insulin in man (Japanese)" XP002566791 Database accession No. EMB-1978092320 abstract & Journal of the Japan Diabetes Society 1977 JP, vol. 20, No. 2, 1977, pp. 146-152, ISSN: 0021-437X.
English translation of the Written Opinion of the International Searching Authority for PCT/FR2010/051426.

* cited by examiner

*Primary Examiner* — Julie Ha
*Assistant Examiner* — Li Ni Komatsu
(74) *Attorney, Agent, or Firm* — Sughrue Mion, PLLC

(57) ABSTRACT

A method and a pharmaceutical composition in the form of a hydroalcoholic solution in which at least one hypoglycemia-inducing/insulinotropic active principle is dissolved in a stable and complete manner at a dosage that is reduced by 30% to 50% compared with the usual oral unit dosage, for its trans-buccal mucosal application in the spot treatment of postprandial hyperglycemia in type II diabetes in man or animals. Also, disclosed is a method of preparing said formulation and to its specific use in the spot treatment of postprandial hyperglycemia (PPHG) in the context of type II diabetes.

9 Claims, No Drawings

METHOD AND PHARMACEUTICAL COMPOSITIONS FOR TRANS-BUCCAL MUCOSA TREATMENT OF POSTPRANDIAL HYPERGLYCAEMIA IN TYPE II DIABETES

CROSS REFERENCE TO RELATED APPLICATIONS

This application is a National Stage of International Application No. PCT/FR2010/051426 filed Jul. 7, 2010, claiming priority based on French Patent Application No. 09 54819 filed Jul. 10, 2009, the contents of all of which are incorporated herein by reference in their entirety.

FIELD OF THE INVENTION

The present invention relates to a method and to compositions for the extemporaneous treatment of postprandial hyperglycemia (PPHG) in type II diabetes by instantaneous systemic administration of at least one hypoglycemia-inducing/insulin-secreting active principle.

In particular, the invention relates to a method of producing and extemporaneously administering a pharmaceutical composition that is exclusive to said application, and to a method of preparing it and to its use.

BACKGROUND OF THE INVENTION

Type II diabetes is an international health scourge that affects more than 300 million subjects throughout the world; it is increasing by 10% to 15% per year.

It is a chronic disease defined by too high a concentration of sugar in the blood, which appears when the pancreas does not secrete enough insulin or when the organism uses the insulin it produces incorrectly. In the long term, the hyperglycemia caused by the excessive presence of glucose in the blood causes certain complications, in particular in the eyes, the kidneys, the nerves, the heart, and the blood vessels.

There are two main types of diabetes.

Diabetes known as type I diabetes or insulin-dependent diabetes is characterized by the insufficient secretion of insulin or by its absence. It is rapidly fatal without the daily administration of insulin by subcutaneous injection(s).

Diabetes known as type II diabetes or adult-onset diabetes is due to poor use of insulin by the organism. It represents 90% of the cases of diabetes in the world and principally results from excess weight and lack of physical exercise.

The physiopathology of type II diabetes associates an anomaly in insulin-sensitivity and in insulin-secretion, in particular a large alteration in the early insulin secretion peak.

An element that has recently been determined as the most actively pathogenic and redolent with vascular, cardiac, and organic consequences in type II diabetes is the existence of a postprandial hyperglycemia (PPHG) peak linked to the absence of an early insulin secretion response.

In the healthy adult, the pancreas produces an early insulin peak that is aimed at metabolizing all of the saturating quantity of glucose absorbed in a rapid cumulative manner during a meal. That early insulin peak can smooth out the sudden variations in glycemia during meals as well as the inevitable consecutive postprandial hyperglycemia. As an example, administration to a non-diabetic person of 20 grams (g) of glucose induces, in a reflex manner, an insulin peak of more than 120 micrograms (μg) per liter (L) of blood in the next 10 minutes (min).

In a type II diabetic person, the same test induces a mean insulin peak of only 35 μg/L of blood, i.e. a 71% deficit, and there is a pathological 30 min delay in its appearance.

Because of that absence of an early response in insulin secretion, per- and post-prandial glycemic variations are not regulated and type II diabetics have to tolerate very high levels of postprandial hyperglycemia of more than 2 g/L to 3 g/L that, even if not felt, represent a hidden danger right from the first stages of the disease.

There are currently several approaches for treating type II diabetes, with the aim of obtaining better control and optimization of glycemia in a stabilized manner, so that thresholds of 1.20 g to 1.40 g of glucose per liter of blood are not exceeded, particularly in the postprandial period. At first, type II diabetes is generally treated by diet and weight loss. Next, if necessary, comes treatment with oral antidiabetics possibly associated with insulin therapy in order to maintain near normal glycemia. The aim of the treatment is to reduce mortality, symptoms, and complications associated with diabetes.

Particular examples of known basic antidiabetics that may be mentioned are hypoglycemia-inducing sulfamides including gliclazide, glibenclamide, and hypoglycemia-inducing biguanides including metformin.

Gliclazide is a lipophilic antidiabetic with a molecular weight of 323 daltons (Da), which is insoluble in water and slightly soluble in alcohol. It acts in the pancreas by stimulating secretions from the islets of Langerhans, increasing the secretion of insulin or peptide C, and also has anti-aggregation type hemato-vascular properties. Currently, gliclazide is administered in unit dosages of 30 milligrams (mg) to 80 mg for 80 mg to 160 mg per day orally. It is extensively metabolized by the first hepatic passage and all of its metabolites are free of activity. With 95% binding to plasma carrier proteins, it has a distribution volume of approximately 30 L, with a plasma peak occurring 11 hours (h) to 14 h after ingestion, and a half-life of 10 h to 12 h.

The other sulfamide, glibenclamide, is a lipophilic active principle that is practically insoluble in water and slightly soluble in ethanol. It is capable of inducing hypoglycemia and is a demonstrated cardiovascular protector. Currently, glibenclamide is administered in unit dosages of 2.5 mg to 5 mg, for on average 10 mg/day (to a maximum of 15 mg/day). It is strongly metabolized by the liver, with a late plasma peak, but has an advantageous effect/dose ratio.

Metformin hydrochloride is a standard amphiphilic antidiabetic with a molecular weight of 165 Da; it is soluble in water and slightly soluble in alcohol. It is a cardiovascular protector that does not act on the pancreatic production of insulin but on the hepatic metabolism of sugar and glycogen, as well as on the use of glucose by tissues. Metformin is currently administered in unit dosages of 500 mg and 1000 mg, for 1000 mg to 3000 mg per day, its absorption being 50% to 60%. It is not bound to plasma proteins and has a distribution volume in the range 63 L to 276 L with a long half-life.

However, although said treatments tend to optimize the glycemia of patients with type II diabetes, none of them takes into account or effectively treats the major and constant problem of the postprandial hyperglycemia (PPHG) peak.

In contrast to type I diabetes, where is it possible to associate a slow release insulin, releasing over 24 h and a rapid-release insulin injected before all meals, guaranteeing a per- and post-prandial insulin peak, which can be adapted by and for each patient, hypoglycemia-inducing treatments proposed for type II diabetes cannot be used to regulate postprandial hyperglycemia in order to keep it close to physiological requirements and international health authority recommendations, namely less than 140 mg of glucose per liter of blood (7.8 nanomoles (nmol) per liter).

The drugs currently used for the chronic treatment of type II diabetes, such as metformin-based drugs, which are all administered orally, offer late activity after taking and a pharmacological availability that remains linear. Thus, they are incapable of reducing, at a given time, the sudden and strong appearance of the postprandial hyperglycemia peak.

However, health authority recommendations concerning the treatment of type II diabetes recognize that the variation in glycemia between "fasting glycemia" and "postprandial glycemia" must not be more than 0.2 g/L to 0.3 g/L, i.e. a very reduced range of fluctuation, which is difficult to obtain with currently available pharmacological means, which are all administered orally and some by injection, which makes therapeutic management by patients more complicated.

For this reason, novel therapeutic classes such as alpha-glucosidase inhibitors, glinides, or gliptins (or incretins) have been developed in order to supplement the constant but insufficient regulatory action of such hypoglycemia-inducing/insulin-secreting agents, administered as a base treatment that remain ill-suited to reducing postprandial hyperglycemia peaks.

Said novel molecules include glinides such as mitiglinide or nateglinide, and in particular repaglinide, which is an oral hypoglycemia-inducing agent that binds to the sulfonylurea receptors of beta pancreatic cells and thus causes rapid short term insulin secretion, capable of responding better to an elevating hyperglycemia. Repaglinide, a derivative of benzoic acid, is a lipophilic molecule with a molecular weight of 452.6 administered in a quantity of 1 mg per meal. The drug has to be taken orally 15 min before each meal three times a day in order to provide better postprandial glycemia control. Repaglinide ingested in that manner causes the onset of an insulinotropic response approximately 30 min after taking it, but with a wide inter-individual variability (60%) in its plasma concentration as well as an intra-individual variability (35%), requiring frequent adjustments in posology. Thus, its digestive absorption and above all its first hepatic passage render its therapeutic efficacy random; these elements alter the immediate pharmacological bioavailability in a variable manner. Thus, that treatment is not satisfactory; moreover, glinides have been shown to cause more hypoglycemia and weight gain than conventional treatments of the metformin type, which is logical since metformin has no insulin-secreting activity.

Incretins or gliptins are intestinal hormones liberated by the endocrinal cells of the intestinal epithelium as nutrients arrive. They play a major role in potentializing the effect of glucose on pancreatic cells. GLP-1 (glucagon-like peptide-1) and GIP (glucose-dependent insulinotropic polypeptide) are the best known. GLP-1 in particular has a strong insulinotropic action in type II diabetic patients. Further, its capacity to stimulate the synthesis of insulin means that it can be used to maintain insulin reserves in beta pancreatic cells. Said effects have been demonstrated by numerous studies carried out in diabetic patients. Even in patients with very high fasting glycemia who no longer respond to conventional hypoglycemia-inducing agents, administering GLP-1 completely normalizes glycemia due to stimulation of the secretion of insulin that is transitional and returns to the base level when normal glycemia is reached. Continuous perfusion of GLP-1 to obese, diabetic patients for a period of 6 weeks causes a reduction in fasting and postprandial glycemia by 4.3 nanomolar (nM) and 5.5 millimolar (mM) respectively. The hemoglobin HbA1C is reduced by 1.3%, with an improvement in sensitivity to insulin and the function of pancreatic beta cells.

However, GLP-1 cannot currently be administered orally because of its peptide nature, and using it requires injection. Furthermore, its in vivo half-life is very short, approximately 1 min to 2 min, due to its rapid degradation by a ubiquitous enzyme, dipeptidylpepditase, which renders it impossible to use. Degradation-resistant forms of GLP-1 have been developed, in particular sitagliptin or vildagliptin or even saxagliptin. Vildagliptin is an amphiphilic molecule that is soluble in water and organic solvents and has a molecular weight of 303.99 Da with a bioavailability of approximately 85%. Sitagliptin is an amphiphilic molecule with a molecular weight of 407.314 Da, which is soluble in water and certain organic solvents; it has an absolute bioavailability of the order of 87%. It is bound to plasma proteins and the mean distribution volume in the organism of a single dose of 100 mg of intravenous sitagliptin is approximately 198 L. Saxagliptin has a molecular weight of 315.41 Da and has a bioavailability that varies in the range 50% to 75% of the orally administered dose; this lipophilic molecule has a high organic distribution volume, close to 180 L. Thus, it can be seen that such molecules have very similar characteristics. However, these peptides, while they improve the overall glycemic profile, always in association with other antidiabetic molecules, cannot overcome the essential problem of type II diabetes, namely compensating for the postprandial hyperglycemia (PPHG) peak during the per/postprandial period; their action on this peak is still marginal.

Thus, none of these novel therapeutic classes is satisfactory. They have insufficient efficacy, are expensive, and some cause tolerance problems or require subcutaneous injections, which presents no advantage over a treatment with insulin that is invasive but would be more effective and more appropriate physiologically.

Thus, the treatment of type II diabetes is currently incomplete and falls short of international recommendations regarding reducing the postprandial hyperglycemia peak. Thus, available therapeutic means are still unsuitable, since there are no drugs that can be used by several hundred million ambulatory patients that can currently combat the PPHG peak to keep it within the recommended limits of a maximum glycemia of less than 1.4 g/L throughout the per/postprandial period.

Thus, there is a substantial need for drugs that can treat the sudden, strong appearance of a PPHG peak, responsible for many medium and long term complications, in particular cardiovascular complications, of type II diabetes.

BRIEF SUMMARY OF THE INVENTION

For this reason, the invention aims to overcome the disadvantages of the prior art by proposing compositions and a method of the administration of insulinotropic pharmaceutical compositions that act rapidly, are easy to use and of moderate price, and that can control peaks in hyperglycemia at mealtimes, a major aim in the treatment of type II diabetes.

To this end, the invention is aimed at a highly specific implementation that can guarantee the instantaneous, transbuccal mucosal administration of an effective dose of at least one hypoglycemia-inducing insulinotropic active principle, more particularly in the spot treatment of postprandial hyperglycemia (PPHG) in type II diabetes in man or animals, by using a hydroalcoholic solution in which at least one hypoglycemia-inducing active principle is dissolved in a stable, complete manner.

The invention also proposes a preparation method as well as the use of said drug for the treatment of type II diabetes in man or animals, specifically the spot treatment necessary to reduce PPHG.

Advantageously, the method and the compositions of the invention induce an instantaneous hypoglycemia-inducing activity equivalent to that which could be obtained by injection. The immediate and complete trans-buccal mucosal passage of a small volume of a therapeutic preparation based on doses of hypoglycemia-inducing/insulinotropic molecules that are at least 30% to 50% lower than those usually delivered orally, while limiting any salivary and swallowing dilution of said molecules means that they are delivered to the vascular system quasi-instantaneously for distribution of the whole dose to specific receptors for their organic pharmacological activity, in order to produce stimulation of the secretion of insulin or to act on neoglucogenesis. The formulation is simple to use, inexpensive, readily available and non-invasive. It can be used to administer an immediately bioavailable quantity of hypoglycemia-inducing/insulinotropic molecules in order to prevent the sudden rise of hyperglycemia, in particular to extemporaneously reduce PPHG in type II diabetes.

In accordance with a further advantage, existing hypoglycemia-inducing/insulinotropic molecules may be used in a far more effective manner at doses by weight reduced by 30% to 50% compared with those administered orally, with the aim of eradicating the PPHG peaks, which peaks have not been able to be treated in the prior art except by injecting insulin. Thus, the invention can provide old, known molecules with a novel, unprecedented therapeutic role, namely the extemporaneous reduction of postprandial hyperglycemia in type II diabetes, an element that is known to be eminently pathogenic but that is currently not actually under therapeutic control.

By providing a means without equivalent in terms of simplicity and medical service, the invention thus satisfies international therapeutic requirements and the requirements of state health authorities without in any way rendering the therapy more complex and the treatment habits of the patients more complicated, i.e. without giving rise to extra costs or constraints such as repeated injection of insulin that is carried out in the treatment of type I diabetes.

DETAILED DESCRIPTION OF THE INVENTION

Further characteristics and advantages become apparent from the following description of the invention.

In a first aspect, the invention thus provides a pharmaceutical composition in the form of a hydroalcoholic solution in which at least one hypoglycemia-inducing/insulinotropic active principle is dissolved in a stable and complete manner, in a dose reduced by at least 30% to 50% compared with that employed for oral administration, for application thereof in the spot treatment of PPHG in type II diabetes. Preferably, the hydroalcoholic has an alcohol content of at least 30°.

The term "transmucosal" means any passive passage of a lipophilic or amphiphilic molecule that is dissolved in a stable and complete manner through the lingual, sublingual, gingival, palate, or cheek mucosae or any other mucosae provided with a lipophilic epithelium and a constituent of the buccal cavity.

The term "dissolved in a stable and a complete manner" means a state of dissolution restoring the active principle to the molecular state, slightly ionized in its dissolving medium, the state of dissolution preventing any possibility of inopportune recrystallization.

The term "hydroalcoholic solution with an alcohol content of at least X" means a solution with an alcohol content of X, corresponding to the ratio between the volume of pure alcohol (100°) contained in the hydroalcoholic solution and the total volume of said solution. The alcohol content of the hydroalcoholic solution varies as a function of the quantity of alcohol used to form the solution and the water/alcohol ratio of the solution. As an example, for an initial alcohol content of 100 degrees and a water/alcohol ratio of 50/50, the hydroalcoholic solution has an alcohol content of 50 degrees alcohol.

In the context of the present invention, the term "reduced dose of hypoglycemia-inducing/insulinotropic active principle" means any lipophilic or amphiphilic active principle that is capable of reducing the quantity of sugar in the blood or of preventing an increase in the quantity of sugar in the blood during the postprandial hyperglycemia (PPHG) peak, said active principle being administered via the buccal mucosae in a fraction that is 30% to 50% smaller than its usual oral unit dosages.

The hypoglycemia-inducing/insulinotropic active principle is present in the form of the base and/or the salt, for example in the form of the succinate, the hydrochloride, the sulfate or the methylsulfate.

The active principle is selected from all lipophilic or amphiphilic hypoglycemia-inducing/insulinotropic active principles with a molecular weight of less than 1000 Da. Non-limiting examples that may be mentioned are hypoglycemia-inducing sulfamides, hypoglycemia-inducing biguanides, glinides and incretins (gliptins).

Particularly suitable hypoglycemia-inducing sulfamides that may be mentioned include gliclazide and glibenclamide.

Particularly suitable hypoglycemia-inducing biguanides that may be mentioned include metformin.

Particularly suitable glinides that may be mentioned include mitiglinide, nateglinide and repaglinide.

Suitable incretins or gliptins that may be mentioned include sitagliptin, vildagliptin and saxagliptin.

In accordance with a particularly suitable embodiment, the pharmaceutical composition of the invention is in the form of a hydroalcoholic solution with a small volume, namely a volume less than 2 mL [milliliter], in which a small quantity of at least one hypoglycemia-inducing active principle is dissolved in a stable and complete manner, namely in a dose that is 30% to 50% lower than the usual orally administered unit dosages or, more generally, less than 250 mg.

The formulation of the invention may optionally also comprise a pH-correcting agent. The term "pH-correcting agent" means any acid or basic acid that does not alter the physicochemical nature of the active principle or active principles.

Preferably, the pH-correcting agent is selected from sodium carbonates and bicarbonates, monosodium or disodium phosphates, triethanolamine, sodium hydroxide (NaOH) and potassium hydroxide (KOH), but also from hydrochloric, sulfuric, phosphoric, citric, malic, lactic, succinic and/or butyric acid.

The composition or formulation may also include, as a function of the active principles under consideration and their specific dosages, an adjuvant element for potentializing dissolution of the active principle, which adjuvant does not intervene in the hypoglycemia-inducing pharmacodynamic activity of the antidiabetic active principle. As an example, it may be tocofersolan or TEPGS, an ester combining two chemical structures, that of vitamin E and polyethylene glycol with a low molecular weight, in the range 1000 Da to 2000 Da.

Preferably, the composition of the invention is in the form of a hydroalcoholic solution comprising 30% to 95% by weight of alcohol and a water content in the range 5% to 70%. More preferably, the formulation of the invention is in the form of a hydroalcoholic solution comprising 40% to 85% by weight of alcohol and a water content in the range 60% to 15%.

The hydroalcoholic solution has an alcohol content of at least 30°, preferably in the range 30° to 90°, more preferably in the range 40° to 60°. This alcohol content is particularly suitable for lipophilic or amphiphilic hypoglycemia-inducing/insulinotropic molecules and means that they can be dissolved in a routinely stable and complete manner and that they are almost instantaneously absorbed through the buccal mucosae Advantageously, the hydroalcoholic solution is the only organic solvent used in the formulation of the invention.

Further, the alcohol in the hydroalcoholic solution does not simply act as a solvent, but also as a promoter of accelerated per-mucosal absorption of the active principle under consideration; the rate of its absorption increases as the alcohol content employed increases. This second role becomes the principal role of the alcohol when the molecules under consideration are far more hydrosoluble than alcohol-soluble.

In a preferred embodiment of the invention, the hydroalcoholic solution is based on water and ethanol.

By way of illustration, it is possible, in accordance with the invention, to obtain complete dissolution of gliclazide, which is rather lipophilic, in an amount of 3.5 mg of gliclazide for 0.75 mL of approximately 50° hydroalcoholic solution.

Similarly, for metformin, complete dissolution of said active principle is obtained, for example, in an amount of 150 mg of metformin for 1 mL of approximately 30° hydroalcoholic solution. Said formulation permits per-mucosal passage of the metformin, which passage would previously have been inconceivable. Clearly, this concentration remains illustrative and susceptible to adaptations as a function of the subjects and the profile of the postprandial hyperglycemia) episodes for their type II diabetes, bearing in mind the wide variability of the doses by weight used for this molecule with multiplicative coefficients of up to six times the unit dosage.

Regarding glibenclamide, a highly soluble active principle, in accordance with the invention, complete dissolution of said active principle can be obtained in an amount of 1 mg of glibenclamide per 1 mL of approximately 50° hydroalcoholic solution. This represents an example of a dosage that can provide a very powerful hypoglycemia-inducing/insulinotropic pharmacodynamic activity without any delay, adapted to respond to the rise in the per/postprandial hyperglycemia peak, while this same active principle is never able to produce this PPHG-reducing activity when administered orally in an amount of only 2.5 mg or 5 mg.

The coefficient of dissolution of the active principles and the useful dosage may thus be adapted by means of the invention by modulating them firstly as a function of the desired alcohol content for an accelerated trans-mucosal passage and secondly as a function of the preferred weight ratio established for each active principle as a function of the water/ethanol equilibrium and any corrective pH adjuvants or adjuvant for dissolutions used.

Preferably, the pH of the formulation of the invention is in the range 4.5 to 9.0, more preferably in the range 4.5 to 8. These pHs promote optimized absorption of the solution.

The formulation of the invention means that the active principle can passively pass through the buccal mucosae in a period of less than 6 seconds after depositing the liquid in contact with a predetermined buccal mucosal surface. The advantage of this very rapid absorption period is that it means that stagnation of the solution and the active principle in the buccal atmosphere is avoided, as well as any accidental mixing with saliva that could alter it, which would introduce a break in the continuity and the stability of dissolution of the active principle or active principles. This short period also means that any reflex swallowing of the solution and the active principle it contains into the digestive tract can be avoided. In addition, the high intravascular concentration of the active principle and its instant distribution have the advantage of providing it with a concentrated pharmacodynamic effect on its pancreatic insulin-secreting receptor target, a "flash" effect that has been inaccessible until now.

The trans-buccal mucosal passage of the active principle presented in the dissolved state in accordance with the invention from the outer epithelial membrane side constituted by phospholipid structures that passively absorb the lipophilic molecules presented in a stable and completely dissolved manner by elective affinity is due to osmotic attraction towards the other side of said membrane, contributed to by the concentration of dissolved active principle and that of the alcoholic solution under consideration. The osmotic attraction is more marked when the alcohol content of the absorption promoter is high. A suitable alcohol content is in the range 30° to 90°, preferably in the range 30° to 65°. This simultaneously provides the best dissolution coefficient as well as particular stabilization for each molecule as well as promotion of its trans mucosal passage in a period of 4 to 6 seconds.

In one embodiment, the invention may be provided by an antidiabetic drug constituted by a hydroalcoholic solution having an alcohol content in the range 30° to 65° in which in the range 3 mg to 10 mg of gliclazide is dissolved. A particularly suitable example that may be mentioned is a hydroalcoholic solution with an alcohol content of 50 comprising 3.5 mg of gliclazide per mL.

In another embodiment, the antidiabetic drug of the invention may be constituted by a hydroalcoholic solution having an alcohol content in the range 40° to 60° with a volume in the range 0.75 mL to 1.5 mL in which in the range 15 mg to 225 mg of metformin is dissolved.

The hypoglycemia-inducing active principle may also be glibenclamide. In particular, the antidiabetic drug of the invention may be constituted by a hydroalcoholic solution having an alcohol content in the range 30° to 65°, in which in the range 0.25 mg to 1 mg of glibenclamide per treatment unit is dissolved.

The active principle may also be selected from among the glinides. In particular, it may be repaglinide. In particular, the antidiabetic drug of the invention may be constituted by a hydroalcoholic solution having an alcohol content in the range 30° to 70° in which in the range 0.05 mg to 1 mg of repaglinide per treatment unit is dissolved.

In another embodiment of the invention, the active principle may be selected from gliptins and incretins. In particular, it may be sitagliptin, vildagliptin or saxagliptin.

In particular, the antidiabetic drug of the invention may be constituted by a hydroalcoholic solution having an alcohol content in the range 30° to 70° in which in the range 0.25 mg to 45 mg of sitagliptin per treatment unit is dissolved. The antidiabetic drug of the invention may also be constituted by a hydroalcoholic solution having an alcohol content in the range 30° to 70° in which in the range 0.25 mg to 25 mg of vildagliptin per treatment unit is dissolved. The antidiabetic drug of the invention may also be constituted by a hydroalcoholic solution having an alcohol content in the range 30° to 70° in which in the range 0.25 mg to 1.5 mg of saxagliptin is dissolved.

The mucosae of the mouth have a very dense network of quasi-spongey micro-vessels and so molecules, both of the alcoholic solvent and the dissolved active principle, which pass through the lipophilic pores of the epithelial membrane are instantly captured by the blood micro-circulation and directed towards the sublingual veins then the jugular veins in the direction of the heart. This phenomenon is accentuated by the presence of alcohol, which causes vasodilation and an increase in the local micro-vascular flux in the mucosae.

Because of this locally elevated circulatory flux, increased by the alcohol, there is never an equilibrium either side of the epithelial membrane: the concentration in the mouth is always higher until the mechanism is exhausted because there are no more molecules to be absorbed.

Thus, with the notable exception of all other "sublingual" forms, all of the alcohol and the active principle dissolved therein in accordance with the invention passes through the mucosae.

Using the galenical form of the invention means that a hypoglycemia-inducing/insulinostimulating dose can be administered passively, it is immediately absorbed as soon as it is deposited in contact with the mucosae, for distribution in an instant via the vascular route, with no delay in its pharmacological action and without being subject to the prior destructive effects of the digestive and hepatic passages. The pharmaceutical composition of the invention can thus be used to provide complete, immediate tissue absorption of the hypoglycemia-inducing molecules, then their distribution in the central circulation of the organism (jugular vein, upper vena cava, right side of heart, pulmonary arteries, lungs, left side of heart, then systemic arterial circulation from the aorta), generating a rapid "flash" type pharmacodynamic response.

As an example, with a galenical form of the invention produced using a composition of 225 mg of metformin dissolved in 1.5 mL of a 30° hydroalcoholic solution of ethanol, all of this very significant dose of metformin can be administered almost instantaneously. This 225 mg dose is close to the maximum theoretically available fraction of a dose that is normally administered orally (500 mg), which represents at best 50% (250 mg) of the dose usually administered orally.

Similarly, with a galenical form of the invention produced from 5 mg of gliclazide dissolved in 1 mL of a 50° ethanol solution, a dose (5 mg for 5 L of blood) that is higher than the maximum theoretically available fraction of a dose normally administered orally can be administered almost instantaneously and passively. In fact, for oral ingestion, in order to obtain a plasma concentration equivalent to 1 mg of gliclazide per liter of blood as with the composition of the invention, 30 mg of gliclazide would be required; its mean distribution volume in the organism would be 30 L.

With the formulation of the invention, the bioavailability of the dose administered by a local per-mucosal route is complete.

The hydroalcoholic solution of the invention, with an alcohol content of at least 30°, not only has the advantage of dissolving the hypoglycemia-inducing/insulinotropic molecules even though they are lipophiles, which promotes their spontaneous per-mucosal absorption, but also it protects the pharmaceutical formulation from microbiological contamination without having to introduce antimicrobial preservation agent(s).

Thus, the hydroalcoholic solution of the invention has a fourfold effect:

it acts as a solvent for the hypoglycemia-inducing active principle, presented in a dose reduced by 30% to 50% compared with that used orally, to treat the PPHG in a person with type II diabetes using lipophilic or amphiphilic molecules with a low molecular weight;

it activates the per-mucosal passage of this dissolved active principle presented at the lipophilic membrane in the molecular state;

the alcohol content has a dual effect on the mucosal absorption rate, both by the osmotic effect and by inducing reflex microvascular vasodilation, which accelerates the local micro-circulatory flux; and it is its own stabilizing agent, which means that the use of conventional additives can be avoided.

Advantageously, the present invention offers great simplicity in production and very good galenical stability: the extremely simplified water/alcohol solution guarantees dissolution of the active principle and means that the excipients normally used for conventional pharmaceutical preparations, including preservatives, can be left out.

Thus, it can both reduce the manufacturing costs and reduce the risks of intolerance and possible interactions between the active principle and the excipients.

In accordance with another advantage, the delays in the pharmacodynamic action of the drug of the invention are very short compared with the slow absorption of existing hypoglycemia-inducing/insulinotropic drugs that require waiting at least 30 min for glinides between taking the drug and the onset of the hypoglycemia-inducing pharmacological action. Thus, it can act without delay in reducing the postprandial hyperglycemia peak.

The near-instantaneous pharmacological delivery means that a patient can self-administer the drug in the per/postprandial period for an effect equivalent to the efficacy of a subcutaneous or intravenous flash injection into the circulation, without the disadvantages of compromising the skin and the iatrogenic risks linked to that type of administration.

It is a drug that can effectively treat a sudden variation in blood glycemia, which none of the prior art drugs or applications could envisage or permit. The invention provides a treatment for postprandial hyperglycemia in the context of a treatment for type II diabetes that is readily available, effective, immediate, simple, and at a reasonable unit cost and therapeutic cost compared with current drugs dealing with this illness.

In addition, the gain in terms of dose/effect ratio compared with existing antidiabetic drugs is at least 84% to 98% for gliclazide, 60% to 93.4% for glibenclamide, 50% to 90% for repaglinide, 50% to 99.75% for sitagliptin and 50% to 99.75% for vildagliptin and 85% to 97.5% for saxagliptin. Administration of the pharmaceutical composition of the invention thus means that savings can be made as indicated in the dosages of each molecule with a therapeutic effect that is obtained instantaneously and a novel therapeutic effect can be obtained that has never been obtained before, namely the spot treatment of postprandial hyperglycemia in a person with type II diabetes. The administered hypoglycemia-inducing/insulinotropic molecules do not encounter any significant obstacles to their instantaneous arterial distribution to their hepatic or pancreatic receptors which they reach in just a few seconds, the base dose that is administered is considerably reduced, comparable to the indispensable bioavailable dose for exerting the required instantaneous theoretical pharmacological activity. This dose is clearly dependent on the administered active principle and the target patient. It is preferably in the range 0.025 mg to 250 mg of active principle, as a function of said active principle under consideration, for volumes of hydroalcoholic solution or 0.25 mL to 2 mL.

Depending on the active principles under consideration, the drug of the invention may be administered in the range 5 min to 15 min after the start of a meal, in order to simulate the first phase of physiological insulinosecretion that is always deficient in the person with type II diabetes, a phase normally occurring a few minutes after the start of the meal but delayed by up to 30 min and 3 times smaller in persons with type II diabetes. The dose of hypoglycemia-inducing/insulinotropic active principle administered in accordance with the invention has the advantage of being directly active in inducing instantaneous stimulation of the production of insulin that is close to normal physiological secretion for some, or an action on the hepatic sugar metabolism and use of glucose by the tissues for others. With glinides, for example, the induced instantaneous stimulation of the production of insulin is very close to the normal physiological production of insulin, which means that the regulation of postprandial hyperglycemia peaks can be infinitely more dynamic and adapted to the patient under consideration; compare this with prior art glinide-based drugs. Further, this insulinotropic competence of the drug of the invention is close to that of an injection of rapid insulin that a diabetic with type I diabetes self-administers subcutaneously a few moments before a meal. In accordance with another advantage, for insulin-secreting hypoglycemiatings and in particular for the glinides, the invention can be used to release insulin both rapidly (a few minutes) and over a short period (1 h to 2 h), expressly corresponding to the recognized duration of the postprandial hyperglycemia peak, with no risk of iatrogenic hypoglycemia.

Further, since the buccal mucosae have an extremely large total absorption surface area, multiplied by the folded nature of its villous tissue, administration of the drug of the invention is free of any risk of inadvertent swallowing or going down the wrong way. In fact, it allows extremely rapid per-mucous passage that prevents any dissolution by saliva or swallowing of the administered active principle with the advantage of not destabilizing the mucosae with various elements or excipients. Further, since it is small in volume, discrete, and easy to administer, the formulation of the invention is particularly suitable for spot ambulatory treatment of postprandial hyperglycemia in type II diabetes that has to be taken several times a day, namely for every meal.

Further, the effects of the alcohol are insignificant. By way of example, 0.75 mL of a hydroalcoholic solution of 50° ethanol could only produce a theoretical circulating alcoholemia of less than 0.017 g/L of blood, using Widmark's official reference formula, i.e. one thirtieth of the legal limit in France, which is 0.5 g/L of blood. Moreover, since its small molecule evaporates spontaneously, the ethanol in the solution administered via the buccal mucosae is exhausted almost entirely early on and spontaneously through the alveolar surfaces of the pulmonary tissue where it has been immediately transported via the pulmonary artery. For this reason, another significant advantage of the administration method of the invention is that there is practically no systemic administration of alcohol.

In a second aspect, the invention provides a method of preparing the formulation.

A particularly suitable method of preparing the product of the invention comprises the following steps:
   mixing alcohol and purified water, preferably in a stainless steel cell, and introducing at least one hypoglycemia-inducing active principle into said mixture, preferably with stirring;
   continuing stirring of the preparation until the active principle is completely dissolved; and
   filtering the solution obtained on a filter with a porosity of 0.45 μm.

In accordance with a preferred implementation, the method comprises the following steps:
   mixing ethanol and purified water and introducing metformin, gliclazide, glibenclamide, repaglinide, sitagliptin or vildagliptin or saxagliptin into said mixture;
   stirring the preparation, preferably for 10 min to 60 min, until a homogeneous suspension is obtained and the active principle is completely dissolved; and
   filtering.

The method may optionally include the following steps before filtering:
   introducing an adjuvant for dissolution; and/or progressively introducing a pH-correcting agent until a desired pH in the range 5.0 to 8.0 is reached;
   continuing stirring, preferably for 5 min to 30 min, until the active principle has completely dissolved; and
   adding water if necessary to make it up to the desired volume.

The present invention may be used in the context of a treatment of type II diabetes for the systemic instantaneous administration of reduced, useful doses of hypoglycemia-inducing agents, in particular of hypoglycemia-inducing sulfamides, hypoglycemia-inducing biguanides, glibenclamide, glinides or incretins, in particular metformin, gliclazide, gibenclamide, repaglinide, sitagliptin or vildagliptin or saxagliptin.

In particular, the present invention may be used to produce a drug for transmucosal buccal administration to counter the appearance of postprandial hyperglycemia peaks in the treatment of type II diabetes and to avoid all of the associated risks.

Such a drug constitutes a simple, effective, exclusive and inexpensive response to the problem of the therapeutic management of postprandial hyperglycemia peaks which until now have been impossible to treat or treated in a marginal manner, with the advantage of being able to use, inter alia, molecules that are already known for their conventional oral administration; thus, most of them have been studied for decades on populations of tens of millions of subjects.

The invention can be used to produce a treatment for type II diabetes, inexistent until now, by administering a hypoglycemia-inducing molecule orally in a treatment that is basically conventional, associated with the administration of an extemporaneous spot treatment of postprandial hyperglycemia (PPHG), by means of a product of the invention dedicated to specifically compensate for the postprandial hyperglycemia peak. It is thus possible to simultaneously treat the two determining aspects of the illness. Thus, the invention provides the therapeutic response that until now has been deficient or insufficient, that of the treatment of postprandial hyperglycemia (PPHG).

The pharmaceutical composition of the invention, corresponding to a very small volume of liquid, is very easy to administer. A patient may readily place it in the mouth, in direct contact with a precise mucosal zone of reduced surface area. Preferably, the patient should deposit the formulation of the invention in a mucous territory away from salivary secretions, for example the vestibule, defined by the lower external gingival crown and by the mucous wall of the lower inner faces of the cheek and lower lip. This channel on average represents a closed reservoir approximately 18 centimeters (cm) long and 1 cm to 1.5 cm deep, i.e. a mucosal absorption area of 35 square centimeters ($cm^2$) to 55 $cm^2$.

In a final aspect, the formulation of the invention requires a specific industrial packaging to allow it to be used safely, simply and ergonomically and to prevent any degradation of the active principle in contact with air or light.

One particular implementation consists in using a packaging, preferably small, plastic or metalloplastic, which may be flexible or formed from glass, opaque, filled in an inert atmospheric such as nitrogen, to protect the stability of the composition and protect it from oxygen and radiation. Such packaging guarantees long-term dissolution and stability of the active principles dissolved in hydroalcoholic solution in accordance with the invention.

Preferably, such packaging comprises a cannula allowing the solution of the invention to be deposited accurately and easily when in contact with a suitable mucosal zone.

For the patient's comfort in use, and for ease of transport, it is preferable to use packaging in the form of specific sealed pouches. Still more preferably, the galenical form of the invention is packaged into unit dosage packs of 0.1 mL to 2 mL, which can provide an accurate, adequate dose of active principle that can be adapted to each patient.

Advantageously, said packaging is easy to transport and the galenical form can readily be used at any time of day.

Several examples of a formulation in accordance with the invention can be mentioned that are particularly capable of producing immediate hypoglycemia-inducing efficacy and can extinguish the PPHG peaks in persons with type II diabetes:

| Formulation 1: 5 mg gliclazide for 1.5 mL of approximately 50° ethanol | |
| --- | --- |
| Gliclazide (active principle): | 5.0 mg |
| Vitamin E TPGS | 3.5 mg |
| NaOH | qs pH 7.5 |
| 95° ethyl alcohol (diluent and absorption promoter): | 0.50 mL |
| purified water (diluent): | qs 1.00 mL |

This first formulation example could be obtained by carrying out the method described below:
 mixing the ethanol and the purified water and introducing the gliclazide and the vitamin E TPGS at the same time into this mixture;
 stirring the preparation, preferably for 10 min to 60 min, until the active principle had completely dissolved; and
 filtering using a 45 μm filter.

| Formulation 2: 3 mg gliclazide for 0.9 mL of approximately 50° ethanol | |
| --- | --- |
| Gliclazide (active principle): | 3.0 mg |
| Vitamin E TPGS | 2.1 mg |
| NaOH | qs pH 7.5 |
| 95° ethyl alcohol (diluent and absorption promoter): | 0.45 mL |
| purified water (diluent): | qs 0.9 mL |

This second formulation example could be obtained by carrying out the method described below:
 mixing the ethanol and the purified water and introducing the Gliclazide and the Vitamin E TPGS at the same time into this mixture;
 stirring the preparation, preferably for 10 min to 60 min, until the active principle had completely dissolved; and
 filtering using a 45 μm filter.

| Formulation 3: 1 mg glibenclamide for 1 mL of approximately 50° ethanol | |
| --- | --- |
| Glibenclamide (active principle): | 1.0 mg |
| NaOH | qs pH 8 |
| 95° ethyl alcohol (diluent and absorption promoter: | 0.5 mL |

| Formulation 3: 1 mg glibenclamide for 1 mL of approximately 50° ethanol | |
| --- | --- |
| purified water (diluent): | qs 1.0 mL |

This third formulation example could be obtained by carrying out the method described below:
 mixing the ethanol and the purified water and introducing the glibenclamide into this mixture;
 adding NaOH to obtain a pH of 8 and stirring the preparation, preferably for 10 min to 60 min, until the active principle had completely dissolved; and
 filtering using a 45 μm filter.

| Formulation 4: 1 mg glibenclamide for 1 mL of approximately 50° ethanol | |
| --- | --- |
| Glibenclamide (active principle): | 1.0 mg |
| Vitamin E TPGS | 2.0 mg |
| NaOH | qs pH 8 |
| 95° ethyl alcohol (diluent and absorption promoter): | 0.30 mL |
| purified water (diluent): | qs 0.75 mL |

This formulation example could be obtained by carrying out the method described below:
This fourth formulation example could be obtained by carrying out the method described below:
 mixing the ethanol and the purified water and introducing the Glibenclamide into this mixture;
 adding Vitamin E TPGS with stirring; and
 then NaOH to obtain a pH of 8 and stirring the preparation, preferably for 10 min to 60 min, until the active principle was completely dissolved.

| Formulation 5: 150 mg for 1 mL of 30° alcohol: | |
| --- | --- |
| Metformin HCl | 150 mg |
| 95° ethyl alcohol (diluent and absorption promoter) | 0.3 mL |
| purified water qs | 1 mL |
| HCl | qs pH 4.6 |

This fifth formulation example could be obtained by carrying out the method described below:
 introducing purified water into a stainless steel cell;
 introducing the metformin with stirring;
 stirring until dissolution is complete;
 adding ethyl alcohol and stirring until a homogeneous solution is obtained at a pH of 4.6; and
 filtering the solution using a 45 μm porosity filter.

| Formulation 6: 0.0625 mg repaglinide for 0.25 mL of 50° hydroalcoholic solution: | |
| --- | --- |
| repaglinide | 0.0625 mg |
| 95° ethyl alcohol | 0.125 mL |
| purified water | 0.125 mL |

This sixth formulation example could be obtained by carrying out the method described below:
 introducing the alcohol and purified water into a stainless steel cell;
 introducing the repaglinide with stirring and maintaining the stirring until dissolution is complete; and filtering the solution using a 45 μm porosity filter.

| Formulation 7: 0.125 mg repaglinide for 0.25 mL of 50° hydroalcoholic solution: | |
|---|---|
| repaglinide | 0.125 mg |
| 95° ethyl alcohol | 0.125 mL |
| purified water | 0.125 mL |

This seventh formulation example could be obtained by carrying out the method described below:
- introducing the alcohol and purified water into a stainless steel cell;
- introducing the repaglinide with stirring and maintaining the stirring until dissolution is complete; and
- filtering the solution using a 45 μm porosity filter.

| Formulation 8: 0.25 mg repaglinide for 0.5 mL of 50° hydroalcoholic solution: | |
|---|---|
| repaglinide | 0.25 mg |
| 95° ethyl alcohol | 0.25 mL |
| purified water | 0.25 mL |

This eighth formulation example could be obtained by carrying out the method described below:
- introducing the alcohol and purified water into a stainless steel cell;
- introducing the repaglinide with stirring and maintaining the stirring until dissolution is complete; and
- filtering the solution using a 45 μm porosity filter.

| Formulation 9: 0.5 mg repaglinide for 1 mL of 50° hydroalcoholic solution: | |
|---|---|
| repaglinide | 0.5 mg |
| 95° ethyl alcohol | 0.50 mL |
| purified water | 0.50 mL |

This ninth formulation example could be obtained by carrying out the method described below:
- introducing the alcohol and purified water into a stainless steel cell;
- introducing the repaglinide with stirring and maintaining the stirring until dissolution is complete; and
- filtering the solution using a 45 μm porosity filter.

| Formulation 10: 5 mg sitagliptin for 0.5 mL of 50° hydroalcoholic solution: | |
|---|---|
| sitagliptin | 5 mg |
| 95° ethyl alcohol | 0.50 mL |
| purified water | 0.50 mL |

This tenth formulation example could be obtained by carrying out the method described below:
- introducing the alcohol and purified water into a stainless steel cell;
- introducing the sitagliptin with stirring and maintaining the stirring until dissolution is complete; and
- filtering the solution using a 45 μm porosity filter.

| Formulation 11: 10 mg sitagliptin for 0.5 mL of 50° hydroalcoholic solution: | |
|---|---|
| sitagliptin | 10 mg |
| 95° ethyl alcohol | 0.25 mL |
| purified water | 0.25 mL |

This eleventh formulation example could be obtained by carrying out the method described below:
- introducing the alcohol and purified water into a stainless steel cell;
- introducing the sitagliptin with stirring and maintaining the stirring until dissolution is complete; and
- filtering the solution using a 45 μm porosity filter.

| Formulation 12: 25 mg sitagliptin for 1 mL of 50° hydroalcoholic solution: | |
|---|---|
| sitagliptin | 25 mg |
| 95° ethyl alcohol | 0.50 mL |
| purified water | 0.50 mL |

This twelfth formulation example could be obtained by carrying out the method described below:
- introducing the alcohol and purified water into a stainless steel cell;
- introducing the sitagliptin with stirring and maintaining the stirring until dissolution is complete; and
- filtering the solution using a 45 μm porosity filter.

| Formulation 13: 2.5 mg vildagliptin for 0.5 mL of 50° hydroalcoholic solution: | |
|---|---|
| vildagliptin | 2.5 mg |
| 95° ethyl alcohol | 0.25 mL |
| purified water | 0.25 mL |

This thirteenth formulation example could be obtained by carrying out the method described below:
- introducing the alcohol and purified water into a stainless steel cell;
- introducing the vildagliptin with stirring and maintaining the stirring until dissolution is complete; and
- filtering the solution using a 45 μm porosity filter.

| Formulation 14: 5 mg vildagliptin for 0.5 mL of 50° hydroalcoholic solution: | |
|---|---|
| vildagliptin | 5 mg |
| 95° ethyl alcohol | 0.25 mL |
| purified water | 0.25 mL |

This fourteenth formulation example could be obtained by carrying out the method described below:
- introducing the alcohol and purified water into a stainless steel cell;
- introducing the vildagliptin with stirring and maintaining the stirring until dissolution is complete; and
- filtering the solution using a 45 μm porosity filter.

| Formulation 15: 10 mg vildagliptin for 1 mL of 50° hydroalcoholic solution: | |
|---|---|
| vildagliptin | 10 mg |
| 95° ethyl alcohol | 0.5 mL |

| Formulation 15: 10 mg vildagliptin for 1 mL of 50° hydroalcoholic solution: | |
| --- | --- |
| purified water | 0.5 mL |

This fifteenth formulation example could be obtained by carrying out the method described below:
- introducing the alcohol and purified water into a stainless steel cell;
- introducing the vildagliptin with stirring and maintaining the stirring until dissolution is complete; and
- filtering the solution using a 45 μm porosity filter.

| Formulation 16: 15 mg vildagliptin for 1 mL of 50° hydroalcoholic solution: | |
| --- | --- |
| vildagliptin | 15 mg |
| 95° ethyl alcohol | 0.5 mL |
| purified water | 0.5 mL |

This sixteenth formulation example could be obtained by carrying out the method described below:
- introducing the alcohol and purified water into a stainless steel cell;
- introducing the vildagliptin with stirring and maintaining the stirring until dissolution is complete; and
- filtering the solution using a 45 μm porosity filter.

| Formulation 17: 1.5 mg saxagliptin for 0.5 mL of 50° hydroalcoholic solution: | |
| --- | --- |
| saxagliptin | 1.5 mg |
| 95° ethyl alcohol | 0.25 mL |
| purified water | 0.25 mL |

This seventeenth formulation example could be obtained by carrying out the method described below:
- introducing the alcohol and purified water into a stainless steel cell;
- introducing the saxagliptin with stirring and maintaining the stirring until dissolution is complete; and
- filtering the solution using a 45 μm porosity filter.

| Formulation 18: 0.75 mg saxagliptin for 0.5 mL of 50° hydroalcoholic solution: | |
| --- | --- |
| saxagliptin | 0.75 mg |
| 95° ethyl alcohol | 0.25 mL |
| purified water | 0.25 mL |

This eighteenth formulation example could be obtained by carrying out the method described below:
- introducing the alcohol and purified water into a stainless steel cell;
- introducing the saxagliptin with stirring and maintaining the stirring until dissolution is complete; and
- filtering the solution using a 45 μm porosity filter.

| Formulation 19: 0.5 mg saxagliptin for 0.5 mL of 50° hydroalcoholic solution: | |
| --- | --- |
| saxagliptin | 0.75 mg |
| 95° ethyl alcohol | 0.25 mL |
| purified water | 0.25 mL |

This nineteenth formulation example could be obtained by carrying out the method described below:
- introducing the alcohol and purified water into a stainless steel cell;
- introducing the saxagliptin with stirring and maintaining the stirring until dissolution is complete; and
- filtering the solution using a 45 μm porosity filter.

| Formulation 20: 0.25 mg saxagliptin for 0.25 mL of 50° hydroalcoholic solution: | |
| --- | --- |
| saxagliptin | 0.25 mg |
| 95° ethyl alcohol | 0.125 mL |
| purified water | 0.125 mL |

This twentieth formulation example could be obtained by carrying out the method described below:
- introducing the alcohol and purified water into a stainless steel cell;
- introducing the saxagliptin with stirring and maintaining the stirring until dissolution is complete; and
- filtering the solution using a 45 μm porosity filter.

Clearly, the invention is not limited to the examples shown and described above, but in contrast encompasses all variations.

The invention is also applicable to animals, in particular to the treatment of overweight pets with type II diabetes, such as dogs, for example.

The invention claimed is:

1. A pharmaceutical composition in the form of a hydroalcoholic solution based on water and ethanol having an ethanol content between 30° and 60° and a water content between 40-70% v/v, wherein said hydroalcoholic solution is the only solvent in said composition, and said hydroalcoholic solution has a volume of less than 2 mL,
   wherein in said hydroalcoholic solution, 250 mg or less of at least one hypoglycemia-inducing active principle is dissolved, for its application by trans-buccal mucosal means as a drug in the spot treatment of postprandial hyperglycemia in type II diabetes in man or animals,
   and wherein the at least one hypoglycemia-inducing active principle is selected from the group consisting of gliclazide, metformin, glibenclamide, glinides, incretins and gliptins.

2. The pharmaceutical composition according to claim 1, wherein the hypoglycemia-inducing active principle is present in the form of a base and/or in the form of a salt.

3. The pharmaceutical composition according to claim 1, wherein the composition further comprises a pH-correcting agent.

4. The pharmaceutical composition according to claim 3, wherein the pH-correcting agent is selected from the group consisting of sodium carbonates and bicarbonates, monosodium or disodium phosphates, triethanolamine, sodium hydroxide, potassium hydroxide, hydrochloric acid, sulfuric acid, succinic acid, butyric acid, phosphoric acid, citric acid, malic acid and lactic acid.

5. The pharmaceutical composition according to claim 1, wherein the composition has a pH in the range of 4.5 to 9.0.

6. A method of preparing a pharmaceutical composition according to claim 1, wherein the method comprises the following steps:

mixing ethanol and purified water and introducing at least one hypoglycemia-inducing insulinotropic active principle into said mixture, wherein the at least one hypoglycemia-inducing active principle is selected from the group consisting of gliclazide, metformin, glibenclamide, glinides, incretins and gliptins;

stirring the preparation until the active principle is completely dissolved; and filtering the solution obtained on a filter with a porosity of 0.45 µm.

7. The method according to claim 6, wherein the method comprises the following steps:

mixing ethanol and purified water and introducing into said mixture at least one hypoglycemia-inducing insulinotropic active principle selected from the group consisting of metformin, gliclazide, glibenclamide, repaglinide, sitagliptin, vildagliptin and saxagliptin;

stirring the preparation for 10 minutes to 60 minutes, until a homogeneous suspension is obtained and the active principle is completely dissolved; and filtering the solution obtained on a filter with a 0.45 µm porosity.

8. The method according to claim 6, further comprising, during the stirring step:

introducing an adjuvant for dissolution;

progressively introducing a pH-correcting agent until a desired pH in the range of 4.5 to 8.0 is reached; and continue stirring for 5 minutes to 30 minutes, until the active principle has completely dissolved.

9. A method for the spot treatment of postprandial hyperglycemia in type II diabetes in humans or animals, comprising trans-buccal mucosal administration the pharmaceutical composition according to claim 1 to a human or animal in need thereof.

* * * * *